US011724098B2

(12) United States Patent
Atherton

(10) Patent No.: US 11,724,098 B2
(45) Date of Patent: Aug. 15, 2023

(54) STEPPER MOTOR DRIVE SYSTEMS AND TUBING OCCLUDER SYSTEM

(71) Applicant: Terumo Cardiovascular Systems Corporation, Ann Arbor, MI (US)

(72) Inventor: James Bradley Atherton, Highland, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 636 days.

(21) Appl. No.: 16/777,533

(22) Filed: Jan. 30, 2020

(65) Prior Publication Data

US 2021/0236704 A1 Aug. 5, 2021

(51) Int. Cl.
*H02P 8/16* (2006.01)
*A61M 60/892* (2021.01)
*H02P 8/12* (2006.01)
*A61M 1/26* (2006.01)
*A61M 1/16* (2006.01)
*A61M 1/36* (2006.01)

(52) U.S. Cl.
CPC ........ *A61M 60/892* (2021.01); *A61M 1/1698* (2013.01); *A61M 1/267* (2014.02); *A61M 1/3666* (2013.01); *H02P 8/12* (2013.01); *H02P 8/16* (2013.01)

(58) Field of Classification Search
CPC ..................................... H02P 8/12; H02P 8/16
See application file for complete search history.

(56) References Cited

U.S. PATENT DOCUMENTS

| | | | | |
|---|---|---|---|---|
| 4,637,817 A | * | 1/1987 | Archibald | ................. F16K 7/06 137/553 |
| 5,977,737 A | | 11/1999 | Labriola, II | |
| 6,129,660 A | * | 10/2000 | Nakazeki | ............ A61M 60/422 623/3.1 |
| 7,774,044 B2 | | 8/2010 | Sauer et al. | |
| 8,814,691 B2 | | 8/2014 | Haddick et al. | |
| 10,013,808 B2 | | 7/2018 | Jones et al. | |
| 10,180,572 B2 | | 1/2019 | Osterhout et al. | |
| 10,197,803 B2 | | 2/2019 | Badiali et al. | |
| 2004/0062060 A1 | | 4/2004 | Komamaki | |
| 2005/0069425 A1 | * | 3/2005 | Gray | ..................... F04B 49/065 417/390 |
| 2005/0206340 A1 | * | 9/2005 | Brundle | ................ A61M 5/142 318/685 |

(Continued)

FOREIGN PATENT DOCUMENTS

| | | |
|---|---|---|
| JP | 2010-504726 | 2/2010 |
| JP | 2016-010599 | 1/2016 |

(Continued)

OTHER PUBLICATIONS

PCT International Search Report and Written Opinion in International Appln. No. PCT/US2021/013094, dated Mar. 16, 2021, 11 pages.

(Continued)

*Primary Examiner* — Rina I Duda
(74) *Attorney, Agent, or Firm* — Fish & Richardson P.C.

(57) ABSTRACT

This document describes stepper motor drive systems. The stepper motor drive systems can be used in many different applications including, for example, to drive a stepper motor of an occluder device in association with a heart-lung machine.

20 Claims, 9 Drawing Sheets

(56) References Cited

U.S. PATENT DOCUMENTS

| | | | |
|---|---|---|---|
| 2006/0025725 | A1 | 2/2006 | Cassidy |
| 2007/0015999 | A1 | 1/2007 | Heldreth et al. |
| 2013/0278631 | A1 | 10/2013 | Border et al. |
| 2015/0002374 | A1 | 1/2015 | Erinjippurath |
| 2015/0055076 | A1* | 2/2015 | Iwamoto .......... G02F 1/134327 349/139 |
| 2017/0160549 | A1 | 6/2017 | Badiali et al. |
| 2017/0103440 | A1 | 7/2017 | Xing et al. |
| 2017/0202633 | A1 | 7/2017 | Liu |
| 2018/0000321 | A1 | 1/2018 | Wales et al. |
| 2018/0082480 | A1 | 3/2018 | White et al. |
| 2018/0147113 | A1 | 5/2018 | Dellimore et al. |
| 2018/0177942 | A1* | 6/2018 | Hirata ............... A61M 5/16804 |
| 2018/0322702 | A1 | 11/2018 | Djajadiningrat |
| 2019/0183576 | A1 | 6/2019 | Fahim et al. |

FOREIGN PATENT DOCUMENTS

| | | |
|---|---|---|
| KR | 2003-0080515 | 10/2003 |
| WO | WO 2003042968 | 5/2003 |
| WO | WO 2012/016062 | 2/2012 |
| WO | WO 2017/033947 | 3/2017 |

OTHER PUBLICATIONS

PCT International Preliminary Report on Patentability in International Appln. No. PCT/US2021/013094, dated Jul. 28, 2022, 9 pages.

JP Office Action in JP Appln. No. 2022-544762, dated Jul. 4, 2023, 6 pages (with English translation).

* cited by examiner

STEPPER MOTOR DRIVE SYSTEMS AND TUBING OCCLUDER SYSTEM

BACKGROUND

1. Technical Field

This document relates to stepper motor drive systems that can be used, for example, to drive a stepper motor of an occluder device in association with a heart-lung machine.

2. Background Information

Hollow fiber oxygenators are utilized within the extracorporeal circuit to meet a patient's gas exchange needs during medical procedures such as cardiopulmonary bypass surgery. Blood from the patient is either gravity drained, or VAVD (vacuum assisted venous drainage) is used to obtain the required amount of flow to maintain sufficient volume in a reservoir. A pump, such as a peristaltic pump or a centrifugal pump coupled with a magnetic drive system, is sometimes used in the main line of the circuit in order to pump blood from the reservoir, through the oxygenator, and finally back to the patient. Flow through such lines can be controlled by adjustably restricting the lines, such as by pinching the lines manually or through the use of a mechanism such as an occluder. Some occluders are driven by stepper motors.

Stepper motors are generally brushless direct current (DC) motors that include a collection of electromagnetic coils. These coils can be energized and de-energized to cause the motor's rotor to rotate in evenly spaced subdivisions of rotation, or "steps". The coils are energized and de-energized by a controller or an external driver circuit. To make the motor shaft turn, a coil is given power, which magnetically attracts the rotor. When the rotor is aligned to the first electromagnet, the next coil is turned on and the first is turned off, the rotor rotates slightly to align with the next coil. This process can then be repeated to control and rotate the rotor to a selected position or rotational distance with a selected speed.

SUMMARY

This document describes stepper motor drive systems that can be used, for example, to drive a stepper motor of an occluder device in association with a heart-lung machine. The stepper motor drive systems described herein can also be beneficially used in many other contexts in which stepper motors are used.

In one aspect, this disclosure is directed to a tube occluder system that includes a tube clamp device configured to releasably receive a tube, a stepper motor having a first winding and a second winding, and arranged to adjust an amount of compression applied to the tube by the tube clamp device, and a drive system electrically coupled to the stepper motor and including a first winding output port configured to electrically connect to a first winding input of the first winding, a first winding input port configured to electrically connect to a first winding output of the first winding, a second winding output port configured to electrically connect to a second winding input of a second winding, a second winding input port configured to electrically connect to a second winding output of the second winding, a first snubber circuit in electrical communication between the first winding input port and the second winding output port, and a second snubber circuit in electrical communication between the second winding input port and the first winding output port.

In some embodiments, the system can include some, all, or none of the following features. The first snubber circuit can include a resistor and a diode in series electrical connection with the resistor, and the diode is configured to pass current from the first winding input port to the second winding output port, and prevent current flow from the second winding output port to the first winding input port. The second snubber circuit can include a resistor and a second diode in series electrical connection with the second resistor, and the second diode is configured to pass current from the second winding input port to the first winding output port, and prevent current flow from the first winding output port to the second winding input port. The tube occluder system can also include a power bus, a first diode configured to pass current from the power bus to the first winding output port, and a second diode configured to pass current from the power bus to the second winding output port. The tube occluder system can also include a low electrical potential power bus, a first switch configured to controllably connect the first winding input port to the low electrical potential power bus, and a second switch configured to controllably connect the second winding input port to the low electrical potential power bus, and at least one resistor configured to limit current flow from the first winding input port to the low electrical potential power bus and to limit current flow from the second winding input port to the low electrical potential power bus.

In another aspect, a method of recirculating energy in a stepper motor can include providing power at a power bus to a first output and to a second output, flowing power through a first electrical load electrically connected to the first output, switching a first switch to block power flow out of the first electrical load to a low electrical potential bus, switching a second switch to permit power from the power bus to flow from the second output, through a second electrical load electrically connected to the second output, to the low electrical potential bus, directing, by a first snubber circuit, power flow out of the first electrical load to the second output, switching the second switch to block power flow out of the second electrical load to the low electrical potential bus, switching the first switch to permit power from the power bus to flow from the first output, though the first electrical load, to the low electrical potential bus, and directing, by a second snubber circuit, power flow out of the second electrical load to the first output. The method can also include preventing backflow of current from the first snubber circuit to the power bus, and preventing backflow of current from the second snubber circuit to the power bus. The first snubber circuit can include a resistor and a diode in series electrical connection with the resistor, wherein directing, by the first snubber circuit, power flow out of the first electrical load to the second output can include permitting, by the diode, power flow from the first electrical load at a first input to the second output, and preventing, by the diode, power flow from the second output to the first input. The second snubber circuit can include a second resistor and a second diode in series electrical connection with the second resistor, wherein directing, by the second snubber circuit, power flow out of the second electrical load to the first output can include permitting, by the second diode, power flow from the second electrical load at a second input to the first output, and preventing, by the second diode, power flow from the first output to the second input. The first electrical load can include a first inductive electrical load, the second electrical load can include a second inductive electrical load, switching the first switch to permit power from the power bus to flow from the first output, though the first electrical load, to the low electrical potential bus can include energizing the first inductive electrical load, and switching the second switch to permit power from the power bus to flow from the second output, through a second electrical load electrically connected to the second output, to the low electrical potential bus can include energizing the second inductive electrical load. Power flow out of the first electrical load to the first output can at least partly include current flow caused by inductance of the first inductive load, and power flow out of the second electrical load to the second output can at least partly include current flow caused by inductance of the second inductive load. The first electrical load can include a first winding of a stepper motor, and the second electrical load can include a second winding of the stepper motor. Switching the first switch to permit power from the power bus to flow from the first output, though the first electrical load, to the low electrical potential bus can include energizing the first winding, and switching the second switch to permit power from the power bus to flow from the second output, through a second electrical load electrically connected to the second output, to the low electrical potential bus can include energizing the second winding. The method can also include controllably switching the first switch and the second switch to urge rotation of the stepper motor in a first direction, actuating, by the stepper motor, a tube clamp device configured to releasably receive a tube, and adjusting, based on the actuation, an amount of compression applied to the tube by the tube clamp device.

In another aspect, an electrical drive system includes a first power output port configured to electrically connect to a first load input of a first electrical load, a first power input port configured to electrically connect to a first load output of the first electrical load, a second power output port configured to electrically connect to a second load input of a second electrical load, a second power input port configured to electrically connect to a second load output of the second electrical load, a first snubber circuit in electrical communication between the first load input port and the second load output port, and a second snubber circuit in electrical communication between the second load input port and the first load output port.

Various embodiments can include some, all, or none of the following features. The first snubber circuit can include a first resistor and a first diode in series electrical connection with the first resistor, and the first diode is configured to pass current from the first load input port to the second load output port, and prevent current flow from the second load output port to the first load input port, and the second snubber circuit can include a second resistor and a second diode in series electrical connection with the second resistor, and the second diode is configured to pass current from the second load input port to the first load output port, and prevent current flow from the first load output port to the second load input port. The system can also include a power bus, a first diode configured to pass current from the power bus to the first load output port, and a second diode configured to pass current from the power bus to the second load output port. The system can also include a low electrical potential power bus, a first switch configured to controllably connect the first load input port to the low electrical potential power bus, and a second switch configured to controllably connect the second load input port to the low electrical potential power bus, and at least one resistor configured to limit current flow from the first load input port to the low electrical potential power bus and to limit current flow from the second load input port to the low electrical potential power bus. At least one of the first electrical load and the second electrical load can be an inductive electrical load. The first electrical load can be a first winding of a stepper motor, and the second electrical load can be a second winding of the stepper motor.

The technology described in this document can be used to provide one or more benefits. For example, in comparison to current systems, the stepper motor drive systems described herein cause stepper motors to exhibit a faster response, such as when accelerating to full speed. For example, in some cases the time required for a stepper motor to reach full speed can about ten times faster using the stepper motor drive systems described herein as compared to current systems.

Additionally, the stepper motor drive systems described herein are more energy efficient than current systems. In other words, the stepper motor drive systems described herein use less electrical energy than in current systems, and dissipate less energy as heat.

Additionally, the stepper motor drive systems described herein are less electrically and mechanically noisy than current systems. In other words, the stepper motor drive systems described herein produce less current ripple, less torque ripple, have lower required working voltages and currents, and have improved electromagnetic compatibility.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes stepper motor drive systems that can be used, for example, to drive a stepper motor of a tube occluder system and device in association with a heart-lung machine. The stepper motor drive systems described herein can also be beneficially used in many other contexts in which stepper motors are used.

Figure 1:
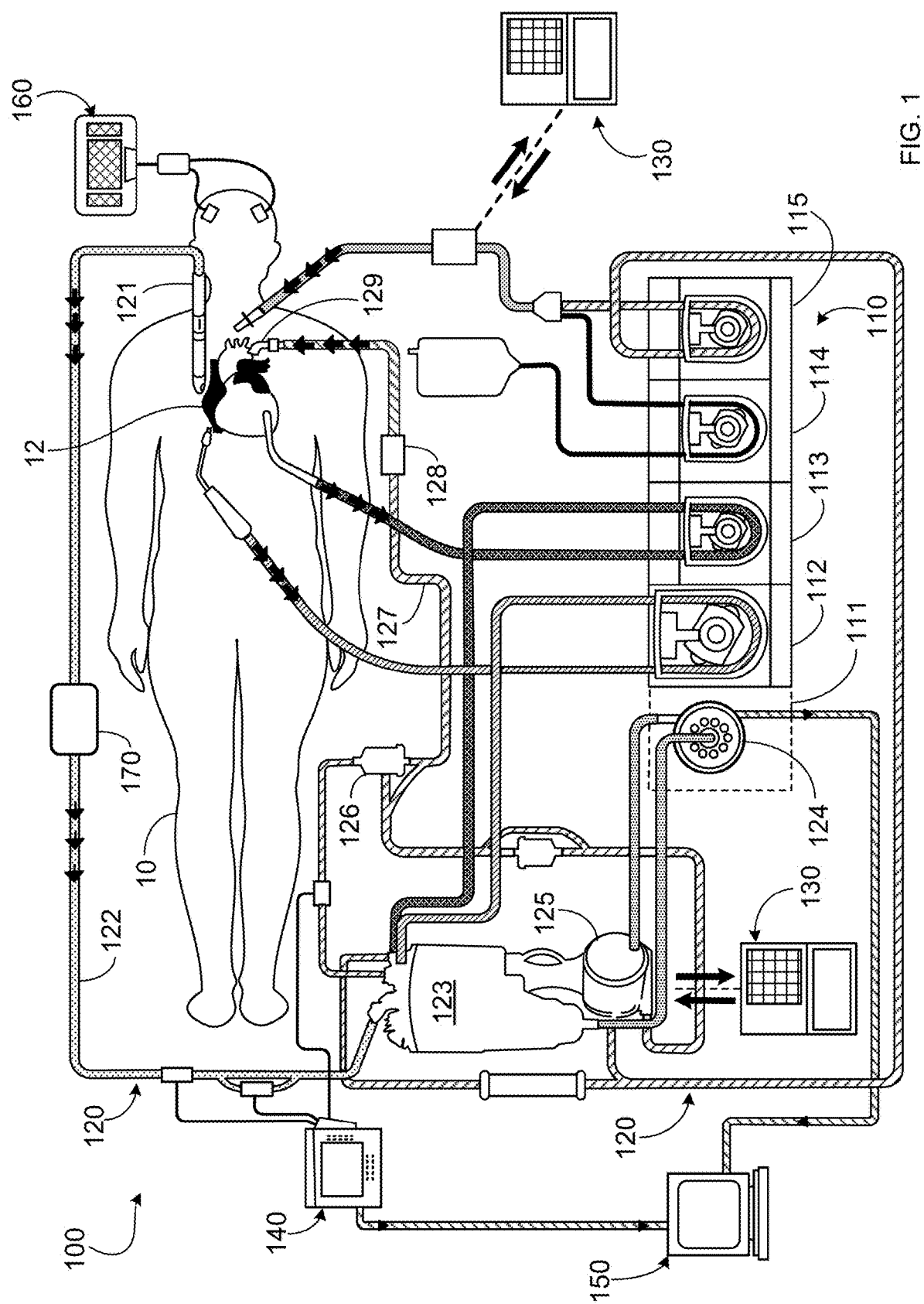
FIG. 1 is a schematic diagram of patient undergoing open-heart surgery while being supported using an extracorporeal circuit in accordance with some embodiments provided herein.

As shown in FIG. 1, various types of medical procedures can be performed on a patient 10 while the patient 10 is connected to a life-sustaining heart/lung bypass machine system 100. In this example, the patient 10 is undergoing open-heart surgery during which the heart 12 and lungs of the patient 10 are temporarily intentionally caused to cease functioning. Because the body of the patient 10 continues to have a metabolic need to receive a supply of circulating oxygenated blood during the medical procedure, however, the heart/lung bypass machine system 100 performs such functions. That is, as described further below, the heart/lung bypass machine system 100 is connected to the patient 10 and performs the functions of the heart 12 and lungs of the patient 10 so that the patient 10 stays alive and healthy during open-heart surgery. The heart/lung bypass machine system 100 can be used for many different types of medical procedures. For example, the medical procedures for which the heart/lung bypass machine system 100 can be used include, but are not limited to, coronary artery bypass grafts, heart valve repairs, heart valve replacements, heart transplants, lung transplants, ablation procedures, repair of septal defects, repair of congenital heart defects, repair of aneurysms, pulmonary endarterectomy, pulmonary thrombectomy, and the like.

In the depicted example, the heart/lung bypass machine system 100 includes components and sub-systems such as a heart/lung machine 110, an extracorporeal circuit 120, one or more temperature control systems 130, a blood monitoring system 140, a perfusion data management system 150, and a regional oximetry system 160. Some types of procedures that use the heart/lung bypass machine system 100 may not require all of the components and sub-systems that are shown. Some types of procedures that use the heart/lung bypass machine system 100 may require additional components and/or sub-systems that are not shown.

The extracorporeal circuit 120 is connected to the patient 10, and to the heart/lung machine 110. Other systems, such as the temperature control system 130, the blood monitoring system 140, and the perfusion data management system 150 may also be arranged to interface with the extracorporeal circuit 120. The extracorporeal circuit 120 is connected to the patient 10 at the patient's heart 12. Oxygen-depleted blood (venous blood) from the patient 10 is extracted from the patient 10 at the patient's heart 12 using a venous catheter 121. As described further below, the blood is circulated through the extracorporeal circuit 120 to receive oxygen and remove carbon dioxide. The oxygenated blood is then returned through the extracorporeal circuit 120 to the patient's heart 12 via an aortic cannula 129.

The extracorporeal circuit 120 can include, at least, a venous tube 122 that is coupled to the venous catheter 121, a blood reservoir 123, a centrifugal pump 124, an oxygenator 125, an arterial filter 126, one or more air bubble detectors 128, and an arterial tube 127 that is coupled to the aortic cannula 129. The venous catheter 121 and venous tube 122 are in fluid communication with the venous side of the circulatory system of the patient 10. The venous tube 122 is also in fluid communication with an inlet to the reservoir 123. An outlet from the reservoir 123 is connected by tubing to an inlet of the pump 124. The outlet of the pump 124 is connected by tubing to an inlet of the oxygenator 125. The outlet of the oxygenator 125 is connected by tubing to an inlet of the arterial filter 126. An outlet of the arterial filter 126 is connected to the arterial tube 127. One or more pressure transducers can be located along the arterial tube 127 to detect a heart/lung machine (HLM) system line pressure of the blood in the arterial tube 127, which is measured by the heart/lung machine 110 and monitored by the perfusionist. The arterial tube 127 is connected to the aortic cannula 129, which is in physical contact with the heart 12 and in fluid communication with the arterial side of the circulatory system of the patient 10.

Briefly, the extracorporeal circuit 120 operates by removing venous, oxygen-depleted blood from the patient 10 via the venous catheter 121, and depositing the venous blood in the reservoir 123 via the venous tube 122. In some cases, gravity is used to cause the blood to flow or drain from the patient 10 to the reservoir 123. In some cases, vacuum is used to assist the blood to flow from the patient 10 to the reservoir 123. At least some amount of blood is intended to be maintained in the reservoir 123 at all times during the surgical procedure. Otherwise, if the reservoir 123 becomes empty, air could be pumped into the extracorporeal circuit 120, and potentially into the vasculature of the patient 10. Such a result would likely be catastrophic for the patient 10. Accordingly, the perfusionist is tasked with visually monitoring the level of the blood in the reservoir 123. In addition, level detectors can be included in conjunction with the reservoir 123 to issue an alarm in response to detection of low-level conditions within the reservoir 123. Moreover, one or more air bubble detectors 128 can be located at various sites along the extracorporeal circuit 120. Blood from the reservoir 123 is drawn from the reservoir 123 by the pump 124. While the depicted embodiment includes a one-time use centrifugal pump as the pump 124, in some cases a peristaltic pump of the heart/lung machine 110 is used instead. The pressure generated by the pump 124 propels the blood through the oxygenator 125. The perfusionist will adjust the pump 124 to operate as desired, while avoiding operational issues such as negative cavitation that could create micro air in the blood of the extracorporeal circuit 120. In the oxygenator 125, the venous blood is enriched with oxygen, and carbon dioxide is removed from the blood. The now oxygen-rich arterial blood exits the oxygenator 125, travels through the arterial filter 126 to remove emboli, and is injected into the patient's heart 12 through the arterial tube 127 via the aortic cannula 129. The extracorporeal circuit 120 can also include tubing and other components for facilitating functions such as, but not limited to, drainage of blood accumulating in the heart of the patient 10, providing surgical suction for maintaining visibility of the surgical field, delivery of cardioplegia solution to the heart 12 of the patient 10 during the procedure, measuring blood parameters, removing air from the blood, hemoconcentration, drug addition, obtaining blood samples, heating and cooling of the blood, and the like.

The heart/lung bypass machine system 100 also includes the heart/lung machine 110. The heart/lung machine 110 is a complex system that includes multiple pumps, monitors, controls, user interfaces, alarms, safety devices, and the like, that are all monitored and operated/adjusted by the perfusionist during a surgical procedure. For example, the depicted heart/lung machine 110 includes an arterial pump 111 (which can be a drive system for a disposable centrifugal pump 124 as shown, or a peristaltic pump), a suction pump 112, a vent/drainage pump 113, a cardioplegia solution pump 114, and a cardioplegia delivery pump 115. The heart/lung machine 110 can also include, or be interfaced with, devices such as a tubing occluder, gas blender, and the like. The parameters of the heart/lung machine 110, such as the rotational speed and other parameters of each of the pumps, are set and adjusted by the perfusionist. For example, the speed of the arterial pump 111 is adjusted to maintain a desirable level of blood in the reservoir 123, and to provide a requisite level of blood circulation within the patient 10.

The heart/lung bypass machine system 100 also includes one or more temperature control systems 130. In a first aspect, the temperature control system(s) 130 is/are used to heat and cool the patient's blood in the oxygenator 125 via a heat exchanger. Additionally, the temperature control system(s) 130 is/are used to heat and cool the cardioplegia solution being delivered to the heart 12 of the patient 10. In general, the temperature control system(s) 130 is/are used in cooling modes during the procedure (to reduce metabolic demands), and subsequently used to warm the blood and/or cardioplegia solution when the surgical procedure is nearing its end. The perfusionist is tasked with monitoring and adjusting the temperature control system(s) 130 as needed during the surgical procedure.

The heart/lung bypass machine system 100, as depicted, also includes the blood monitoring system 140. The blood monitoring system 140 is used to monitor the extracorporeal blood of the patient 10 during the surgical procedure. Parameters being monitored can include, but are not limited to, pH, $pCO_2$, $pO_2$, K+, temperature, $SO_2$, hematocrit, hemoglobin, base excess, bicarbonate, oxygen consumption and oxygen delivery.

The heart/lung bypass machine system 100, as depicted, also includes the perfusion data management system 150 and the regional oximetry system 160. These systems can also be used by the perfusionist to monitor the status of the patient 10 and/or the status of the heart/lung bypass machine system 100 during surgical procedures.

The heart/lung bypass machine system 100, as depicted, also includes an occluder device 170 (e.g., a tube occluder system). In the depicted example arrangement, the occluder device 170 is located along the venous tube 122. Alternatively, or additionally, the occluder device 170 can be located along the arterial tube 127 or any other tube of the heart/lung bypass machine system 100. The occluder device 170 applies an external clamping force to the outer diameter of the tube to modulate a flow rate of the fluid flowing in the tube. In some cases, the occluder device 170 is used as a shut-off device that can be activated to occlude the tube completely, thereby preventing all flow of fluid through the tube.

Figure 2:
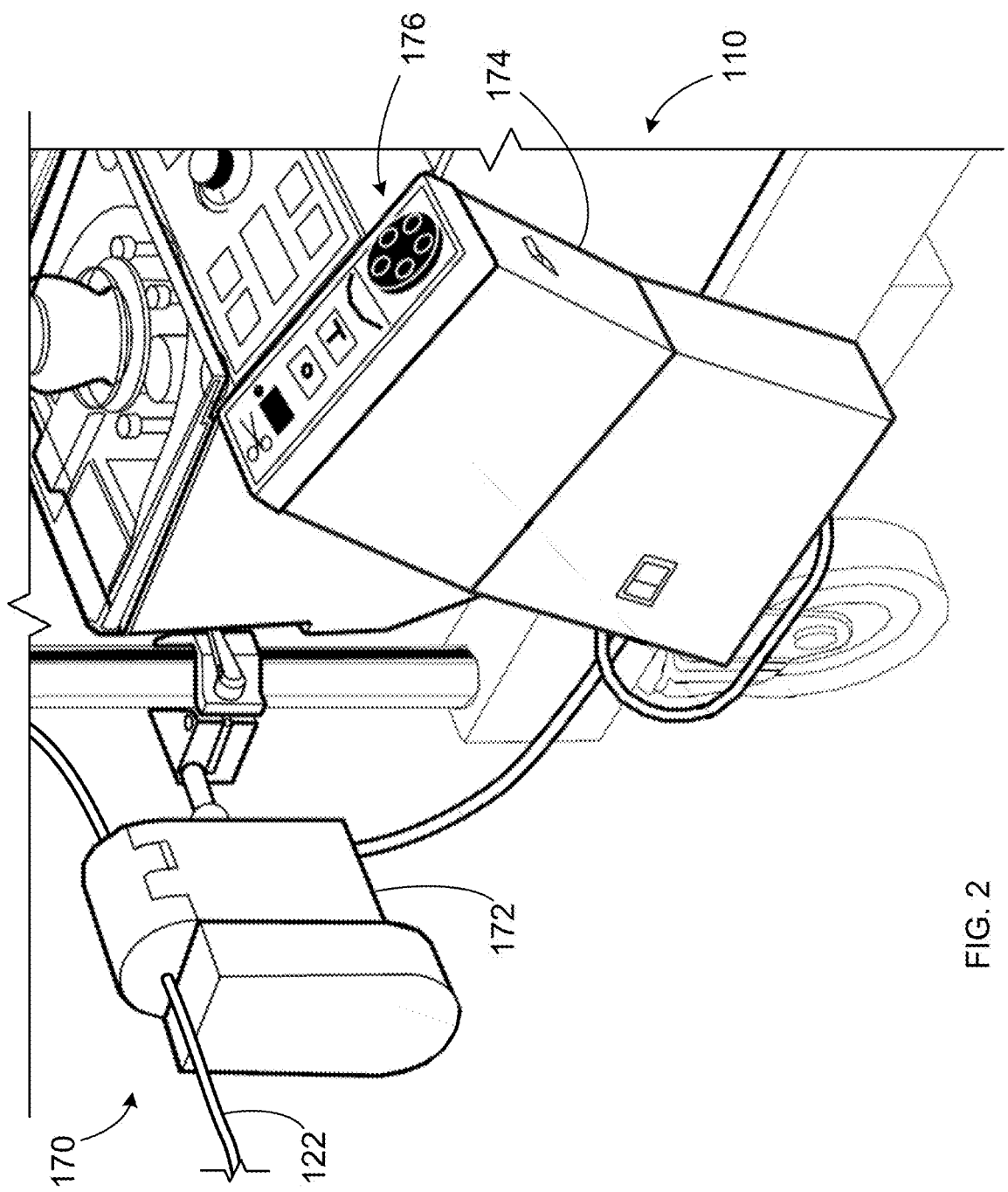
FIG. 2 illustrates a portion of a heart-lung-machine and a tube occluder device in accordance with some embodiments.

Referring now also to FIG. 2, in this example the occluder device 170 is shown as being mounted to the heart/lung machine 110. The occluder device 170 includes an occluder housing 172, a drive system housing 174, and a user interface 176.

The occluder housing 172 is configured to releasably receive a tube (in this example the tube is venous tube 122). Within the occluder housing 172 is a clamp mechanism (not visible) that compresses the outer diameter of the tube 122 and a stepper motor (not visible) that drives the clamp mechanism. The stepper motor can be operated to adjust a controlled amount of compression applied to the tube 122 to modulate the flow of fluid through the tube 122.

Within the drive system housing 174 is a stepper motor drive system (not visible) that is electrically coupled to the stepper motor. The stepper motor drive system is described further below.

The occluder device 170 also includes the user interface 176. The user (e.g., perfusionist) can adjust the flow rate of the fluid in the tube 122 via the user interface 176.

Figure 3:
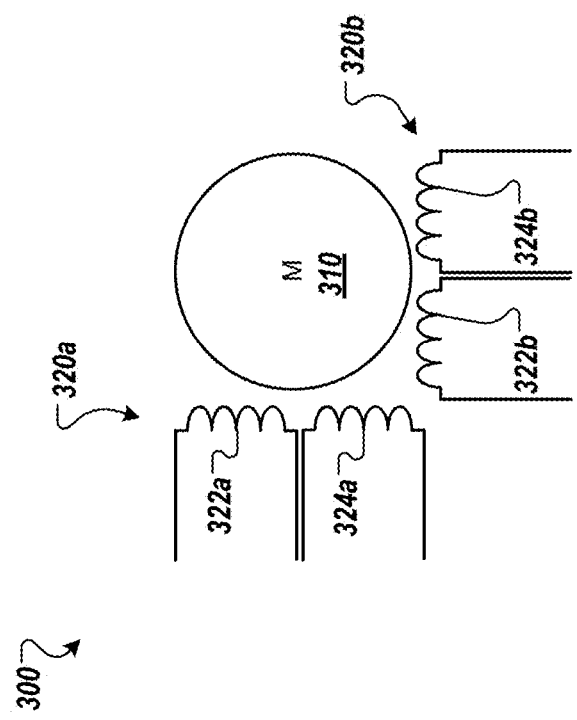
FIG. 3 is a schematic diagram of a prior art stepper motor.

Referring to FIG. 3, a schematic diagram of an example stepper motor 300 is shown. The stepper motor 300 includes a rotor 310, a phase 320a, and a phase 320b. In the illustrated example, the stepper motor 300 is an eight-wire unipolar stepper motor, in which the phase 320a includes a winding 322a and a winding 324a, and the phase 320b includes a winding 322b and a winding 324b. Each of the coils 322a, 322b, 324a, and 324b has a coil input and a coil output. In some embodiments, unipolar stepper motors have one winding per phase, each with a center tap, and each section of the windings can be energized for each direction of magnetic field. Typically, given a phase, the center tap of each winding is made common, which results in three leads per phase and six leads total (e.g., for a two phase motor). In some embodiments, the two center taps can be internally joined, resulting in a five-wire configuration. In some embodiments, the stepper motor 300 can be a bipolar stepper motor, with a single coil per phase.

In use, the windings 322a, 322b, 324a, and 324b of the phases 320a and 320b can be controllably energized and de-energized (e.g., under control of a motor controller), to urge rotation of the rotor 310. When energized, an electrical coil, such as each of the windings 322a, 322b, 324a, and 324b, does not flow current instantaneously. Rather, the current flow starts relatively slowly and builds to its maximum flow as the magnetic fields generated by the current flow through the coil build to their maximum. Conversely, current flow through a coil does not stop instantaneously when the coil is de-energized. The collapsing magnetic field will continue to urge current flow until it falls to zero.

Figure 4:
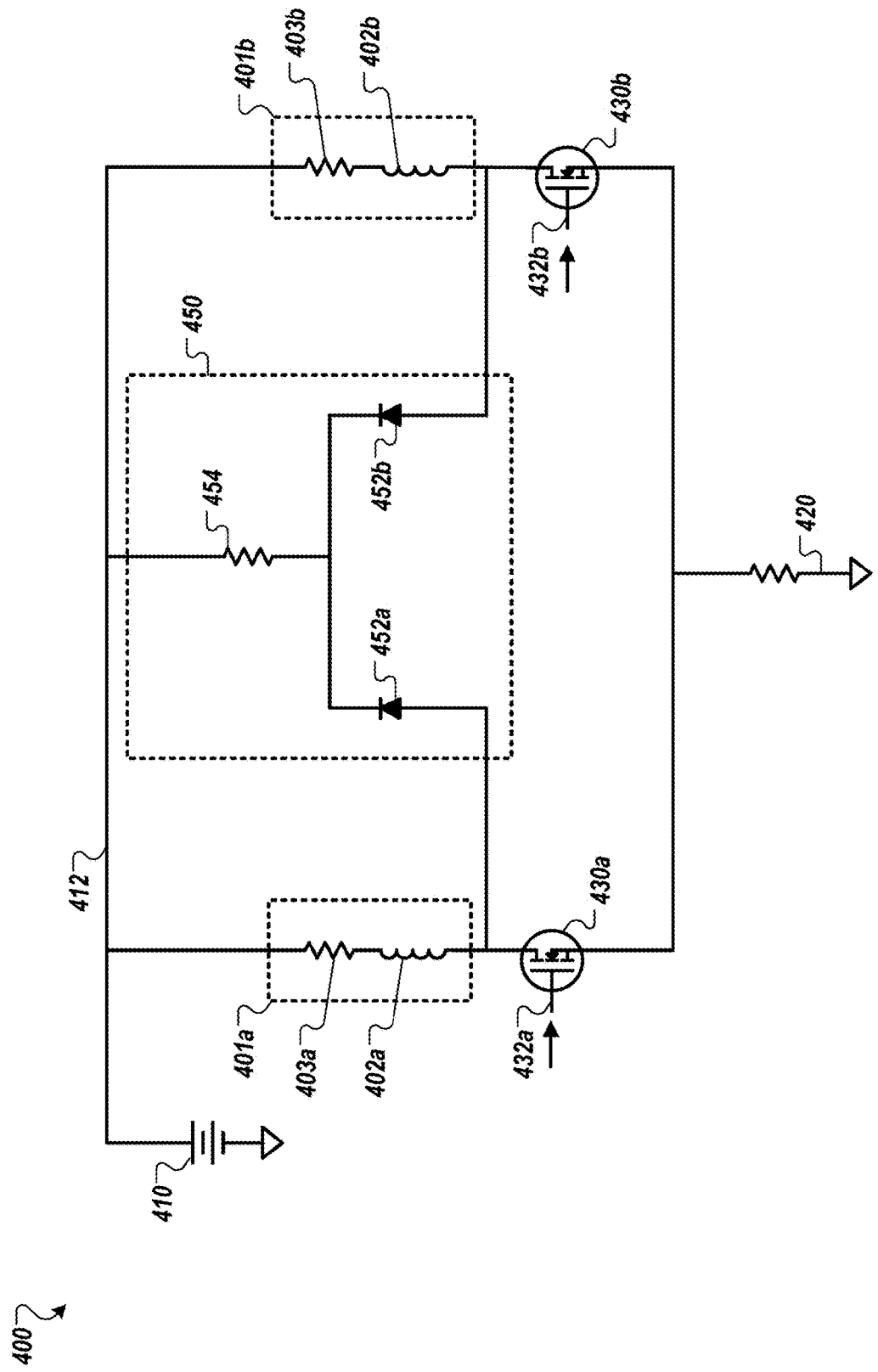
FIG. 4 is a schematic diagram of a prior art motor driver circuit.

Referring to FIG. 4, a schematic diagram of a prior art motor driver circuit 400 is shown. The circuit 400 is configured to drive a winding 401a and a winding 401b of a stepper motor. In some implementations, the winding 401a and the winding 401b can be all or part of the example phase 320a or the phase 320b of the example stepper motor 300 of FIG. 3.

The winding 401a includes a coil 402a and a resistor 403a. In some embodiments, the coil 402a can model the inductance of the winding 401a. In some embodiments, the resistor 403a can model the inherent DC resistance of the winding 401a. The winding 401b includes a coil 402b and a resistor 403b. In some embodiments, the coil 402b can model the inductance of the winding 401b. In some embodiments, the resistor 403b can model the inherent DC resistance of the winding 401b. The coil 402a is part of an electromagnet that drives a winding of the stepper motor, and the coil 402b is part of an electromagnet that drives another winding of the stepper motor. Winding inductance is typically specified in a stepper motor's datasheet so the designer can have some idea how long it takes to build up energy in the winding, and this can be approximated by a first order differential equation where tau=L/R, L the winding inductance and R the winding resistance (DCR) (e.g., winding_current(time)=(Vsupply/DCR)*(1−e^−t/tau)).

A power supply 410 provides power to a power bus 412. The power bus 412 provides power to the winding 401a and the winding 401b. Electrical current flow from the power bus 412 though the winding 401a to a low electrical potential bus 420 (e.g., ground, neutral, negative) is controllably blocked and permitted by a switch 430a based on control signals provided to a switch input 432a. Electrical current flow from the power bus 412 though the winding 401b to the low electrical potential bus 420 is controllably blocked and permitted by a switch 430b. In the illustrated example, the switches 430a and 430b are MOSFET devices.

By controllably alternating the flow of power through the switches 430a and 430b, the windings 401a and 401b can be energized and de-energized to urge rotation of the stepper motor. As mentioned above, current flow through a coil does not stop instantaneously when power is switched off. Instead, there is a residual current flow that is induced by the collapsing magnetic fields around the coil(s). In the illustrated example, such currents can cause voltage spikes across the switches 430a and 430b, and such voltage spikes can damage the switches 430a and 430b (e.g., due to electrical arcing) if not accounted for with a snubber circuit 450.

In the example of FIG. 4, the snubber circuit 450 is a known snubber circuit configuration. When the switch 430a is shut off, residual current from the winding 401a is prevented from flowing to the low electrical potential bus 420. The residual current of the winding 401a is able to flow from the winding 401a back to the power bus 412 through a diode 452a and a current dissipating resistor 454. The diode 452a prevents current from the power bus 412 from bypassing the winding 401a. When the switch 430b is shut off, residual current from the winding 401b is prevented from flowing to the low electrical potential bus 420. The residual current of the winding 401b is able to flow from the winding 401b back to the power bus 412 through a diode 452b and the current dissipating resistor 454. The diode 452b prevents current from the power bus 412 from bypassing the winding 401b.

In general, the residual energy that flows through the snubber circuit 450 is dissipated (e.g., turned into heat) by the current dissipating resistor 454. In the example of the circuit 400, the residual energy is lost through the dissipation, and can have unwanted effects, such as the generation of heat. In the example of the circuit 400, the speed at which the coils 402a, 402b is proportional to the amount of power available at the power bus 412. For example, if the coils 402a, 402b need to be energized more quickly (e.g., for greater assurance that the stepper motor 300 will not stall, to create less current and/or torque ripple), the output of the power supply 410 would need to be increased (e.g., resulting in increased size, cost, weight of the circuit 400), and as the amount of power being switched by the switches 430a, 430b increases, the amount of electromagnetic interference (EMI) (e.g., switching noise) can increase, and may need to be addressed depending on the application (e.g., further increasing the size, cost, and complexity of the circuit 400).

Figure 5:
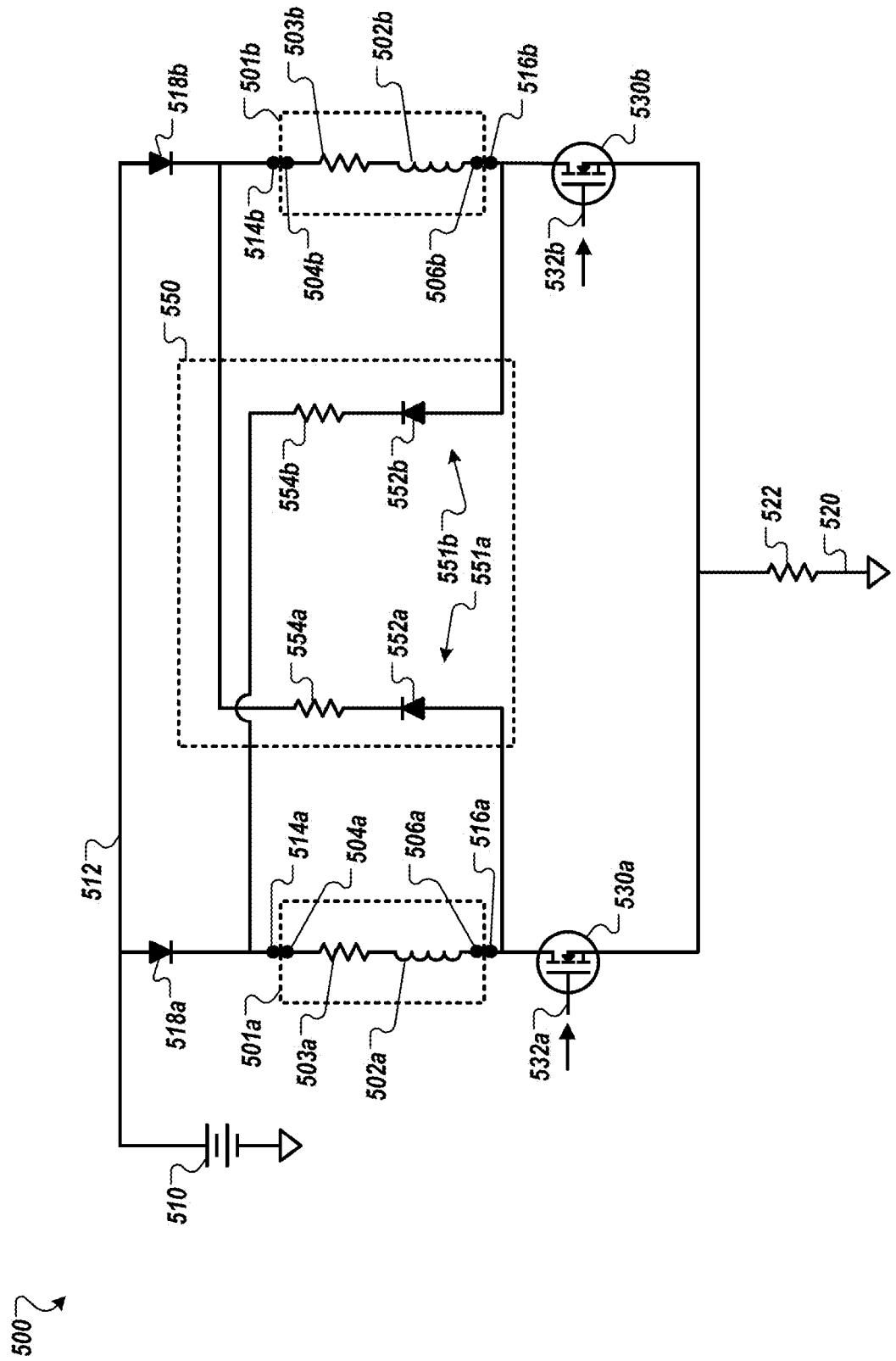
FIG. 5 is a schematic diagram of an example motor driver circuit in accordance with some embodiments.

Referring to FIG. 5, a schematic diagram of an example motor driver circuit 500 is shown, in accordance with some embodiments disclosed herein. The circuit 500 is configured to drive a winding 501a and a winding 501b of a stepper motor. In some implementations, the winding 501a and the winding 501b can be analogous to any two of the example windings 322a, 322b, 324a, and t 324b of the example stepper motor 300 of FIG. 3.

The winding 501a includes a coil 502a and a resistor 503a. In some embodiments, the coil 502a can model the inductance of the winding 501a. In some embodiments, the resistor 503a can model the inherent DC resistance of the winding 501a. The winding 501b includes a coil 502b and a resistor 503b. In some embodiments, the coil 502b models the inductance of the winding 501b. In some embodiments, the resistor 503b can model the inherent DC resistance of the winding 501b. The coil 502a is part of an electromagnet that drives a motor winding of a stepper motor (e.g., the example stepper motor 300), and the coil 502b is part of an electromagnet that drives another motor winding of the same phase or a different phase of the stepper motor.

A load input port 504a is configured to receive electrical power into the winding 501a, and a load output port 506a is configured to permit electrical power to flow out of the winding 501a. In the illustrated example, the load input port 504a is a stepper motor winding input port or input lead wire, and the load output port 506a is a stepper motor winding output port or output lead wire.

A power supply 510 provides power to a power bus 512. The power bus 512 provides power to a load output port 514a and a load output port 514b. The load output port 514a is configured to connect to the load input port 504a electrically, and the load output port 514b is configured to connect to the load input port 504b electrically. A load input port 516a is configured to electrically connected to the load output port 506a to receive power flowing out from the winding 501a. A load input port 516b is configured to electrically connected to the load output port 506b to receive power flowing out from the winding 501b. Current backflow to the power bus 512 is blocked by a diode 518a arranged between the load output port 514a and the power bus 512. Current backflow to the power bus 512 from the winding 501a is blocked by a diode 518a arranged between the load output port 514a and the power bus 512. Current backflow to the power bus 512 from the winding 501b is blocked by a diode 518b arranged between the load output port 514b and the power bus 512. In some embodiments, the diodes 518a, 518b can be omitted, for example, when the power supply 510 is a unidirectional power supply. In some embodiments, the diodes 518a and 518b can replaced by a single diode, e.g., in the case of a 6-leaded stepper motor, where the power supply is bidirectional. In some embodiments, the diodes 518a and 518b can be removed in the case of a 6-leaded stepper motor, e.g., if the power supply is unidirectional. In some embodiments in which an 8-leaded stepper motor is used, the diodes 518a and 518b can both be used, regardless of whether the power supply 410 is unidirectional and/or bidirectional.

The circuit 500 includes a low electrical potential bus 520. In the illustrated example, the low electrical potential bus 520 is a ground bus, but in some embodiments the low electrical potential bus 520 can include a neutral line, a negative (e.g., return) line, or can be at any appropriate voltage that is less than the voltage of the power bus 512.

Electrical current flow from the power bus 512 though the winding 501a to the low electrical potential bus 520 is controllably blocked and permitted by a switch 530a based on control signals provided to a switch input 532a. Electrical current flow from the power bus 512 though the winding 501b to the low electrical potential bus 520 is controllably blocked and permitted by a switch 530b. In the illustrated example, the switches 530a and 530b are MOSFET devices, but in some embodiments the 530a and 530b the switches can be any appropriate form of controllable switch that can control current flow though the windings 501a and 501b (e.g., FETs, IGBTs, BJTs, or other forms of transistors, relays). A current-limiting resistor 522 limits current flow to the low-potential bus.

By controllably alternating the flow of power through the switches 530a and 530b, the windings 501a and 501b can be energized and de-energized to urge rotation of the stepper motor. As mentioned above, current flow through a coil does not stop instantaneously when power is switched off; there is a residual current flow that is induced by the collapsing magnetic fields around the coil(s) 502a, 502b. In the illustrated example, such currents that could otherwise cause voltage spikes across the switches 530a and 530b (and possibly damage the switches 530a and 530b due to electrical arcing, for example) are accounted for with a snubber circuit 550.

The snubber circuit includes a branch 551a and a branch 551b. The branch 551a provides electrical communication between the load input port 516a to the load output port 514b. The branch 551a includes a diode 552a in series connection with a current limiting resistor 554a. The diode 552a is configured to permit current flow from the load input port 516a to the load output port 514b, and prevent current flow from the load output port 514b to the load input port 516a. The branch 551b provides electrical communication between the load input port 516b to the load output port 514a. The branch 551b includes a diode 552b in series connection with a current limiting resistor 554b. The diode 552b is configured to permit current flow from the load input port 516b to the load output port 514a, and prevent current flow from the load output port 514a to the load input port 516b.

In use, the switch 530a is turned on and the winding 501a becomes energized, while the switch 530b is off. The switch 530a is then turned off. A residual current will be pushed out of the coil 502a. Backflow of this residual current is blocked by the diode 518a and the diode 552b. Forward flow of this residual current is blocked by the switch 530a, leaving the branch 551a as the only electrical path where the residual current can flow. As the coil 502a de-energizes, the residual current flows though the branch 551a to the load output port 514b. The diode 518b prevents current backflow to the power bus 512, so the current flows into the winding 501b to the coil 502b. In the illustrated example, the residual current created as the coil 502a de-energizes is used to energize the coil 502b to at least a partial degree. In some implementations, the snubber circuit 550 can recapture the energy of the coil 502a (e.g., rather than dissipate it) and use that recaptured energy, along with power from the power bus 512, to energize the coil 502b more quickly than it could be energized based on power from the power bus 512 alone.

Continuing the previous example, in use, the switch 530b is turned on and the winding 501b becomes energized, and the switch 530a is turned off. The switch 530b is then turned off. A residual current will be pushed out of the coil 502b. Backflow of this residual current is blocked by the diode 518b and the diode 552a. Forward flow of this residual current is blocked by the switch 530b, leaving the branch 551b as the only electrical path where the residual current can flow. As the coil 502b de-energizes, the residual current flows though the branch 551b to the load output port 514a. The diode 518a prevents current backflow to the power bus 512, so the current flows into the winding 501a to the coil 502a. In the illustrated example, the residual current created as the coil 502b de-energizes is used to energize the coil 502a to at least a partial degree. In some implementations, the snubber circuit 550 can recapture the energy of the coil 502b (e.g., rather than dissipate it) and use that recaptured energy, along with power from the power bus 512, to energize the coil 502a more quickly than it could be energized based on power from the power bus 512 alone.

In some implementations, by redirecting residual energy from the coils 502a, 502b to their counterpart coil, energy efficiency can be increased. For example, at least a portion of the residual coil energy can be reused instead of being entirely dissipated.

In some implementations, by redirecting residual energy from the coils 502a, 502b to their counterpart coil, temperatures and/or the need for thermal management can be reduced. For example, the circuit 500 does not implement a current dissipating resistor such as the current dissipating resistor 454 of FIG. 4, which dissipates residual coil energy as heat. Since the circuit 500 substantially recycles coil energy, rather than substantially dissipate the energy as heat, the thermal management associated with such heat generation is substantially reduced.

In some implementations, by redirecting residual energy from the coils 502a, 502b to their counterpart coil, the circuit 500 can be implemented efficiently (e.g., more efficiently than the example circuit 400). For example, in the example of the circuit 400, in order to increase the rate at which the coils 402a, 402b are energized, the capacity of the power supply 410 and/or the power bus 412 would need to be increased, which could increase the size, weight, cost, and/or complexity of the circuit 400. Unlike the circuit 400, the circuit 500 is configured to use residual energy from one of the coils 502a, 502b in addition to power from the power bus 512 to energize the other one of the coils 502a, 502b. As such, the performance of the coils 502a, 502b can be increased (e.g., for greater assurance that the stepper motor will not stall, to create less current and/or torque ripple) without the size, weight, cost, and/or complexity that may be associated with achieving similar performance increases by increasing the capacity of the power supply 510 and/or the power bus 512.

In some implementations, by redirecting residual energy from the coils 502a, 502b to their counterpart coil, electromagnetic interference (EMI) and/or and the need for EMI management can be reduced. For example, residual energy in the coils 502a, 502b is redirected away from the switches 530a, 530b relatively more quickly than in the circuit 400, resulting is relatively lower voltages across the switches 530a, 530b. The relatively lower voltages provided by the snubber circuit 550 can result in relatively lower amounts of EMI (e.g., switching noise) caused by switching of the switches 530a, 530b, relative to the circuit 400.

Figure 6:
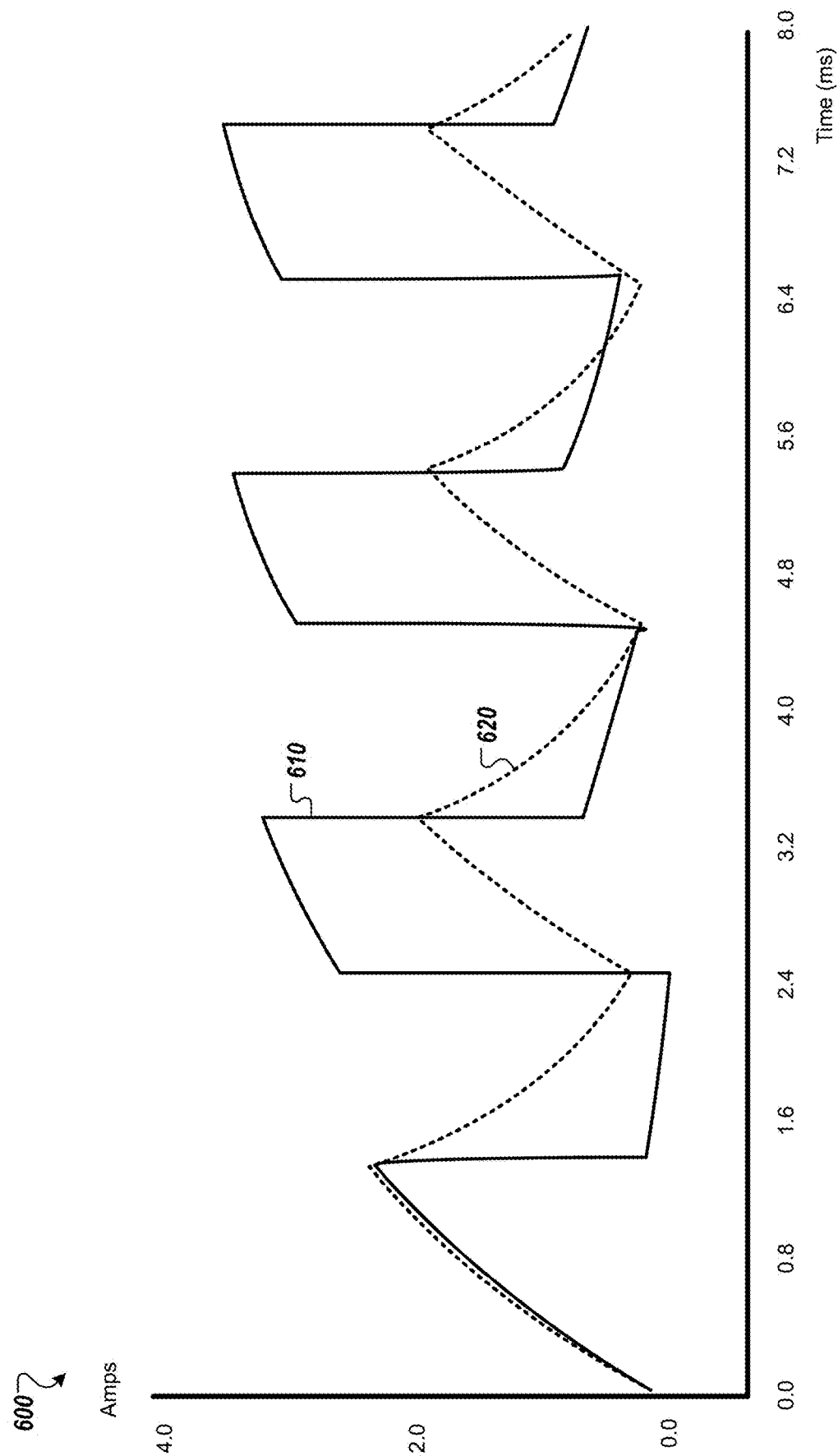
FIGS. 6-8 are charts of example motor driver electrical waveforms in accordance with some embodiments.
Figure 7:
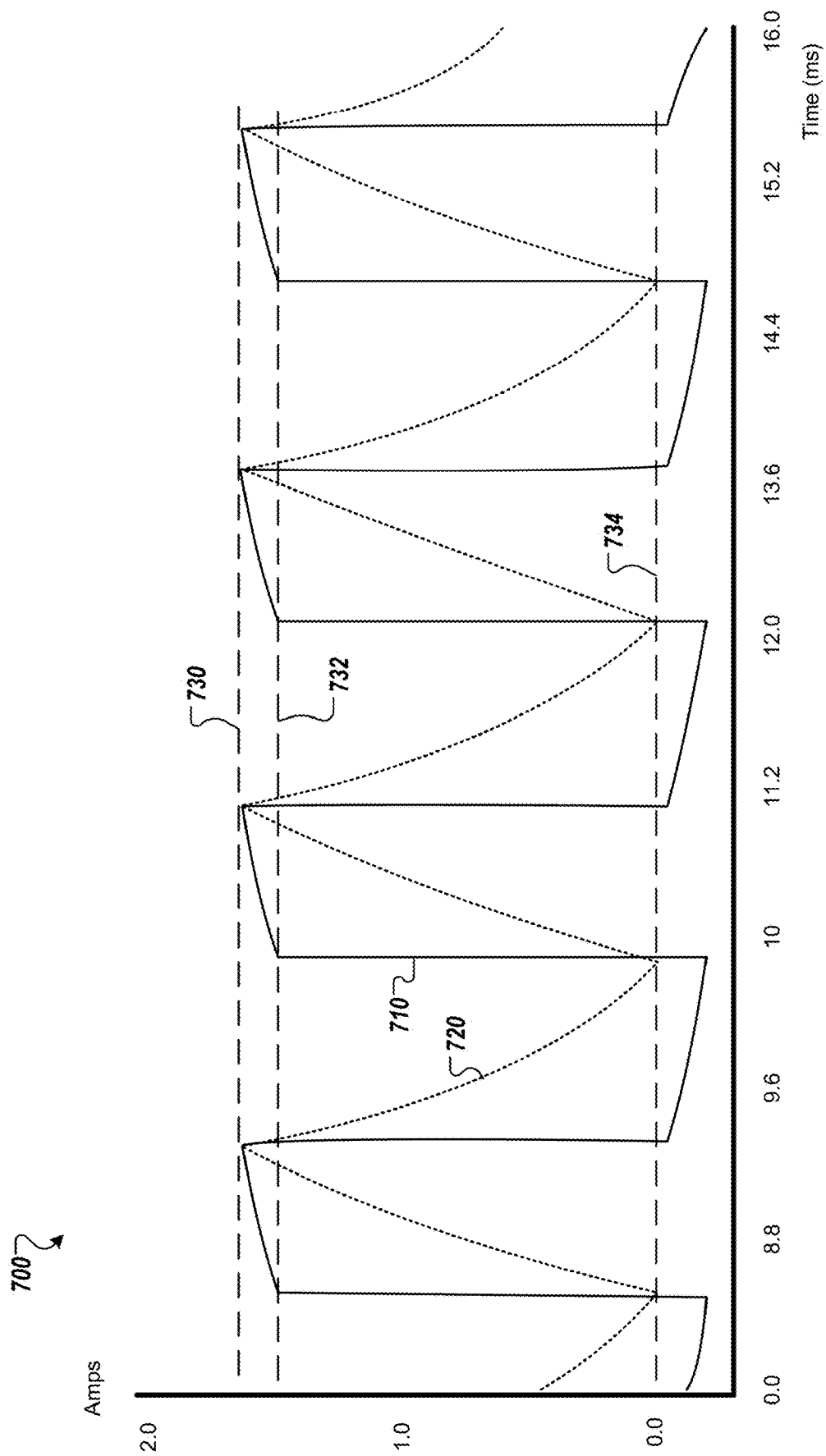
Figure 8:
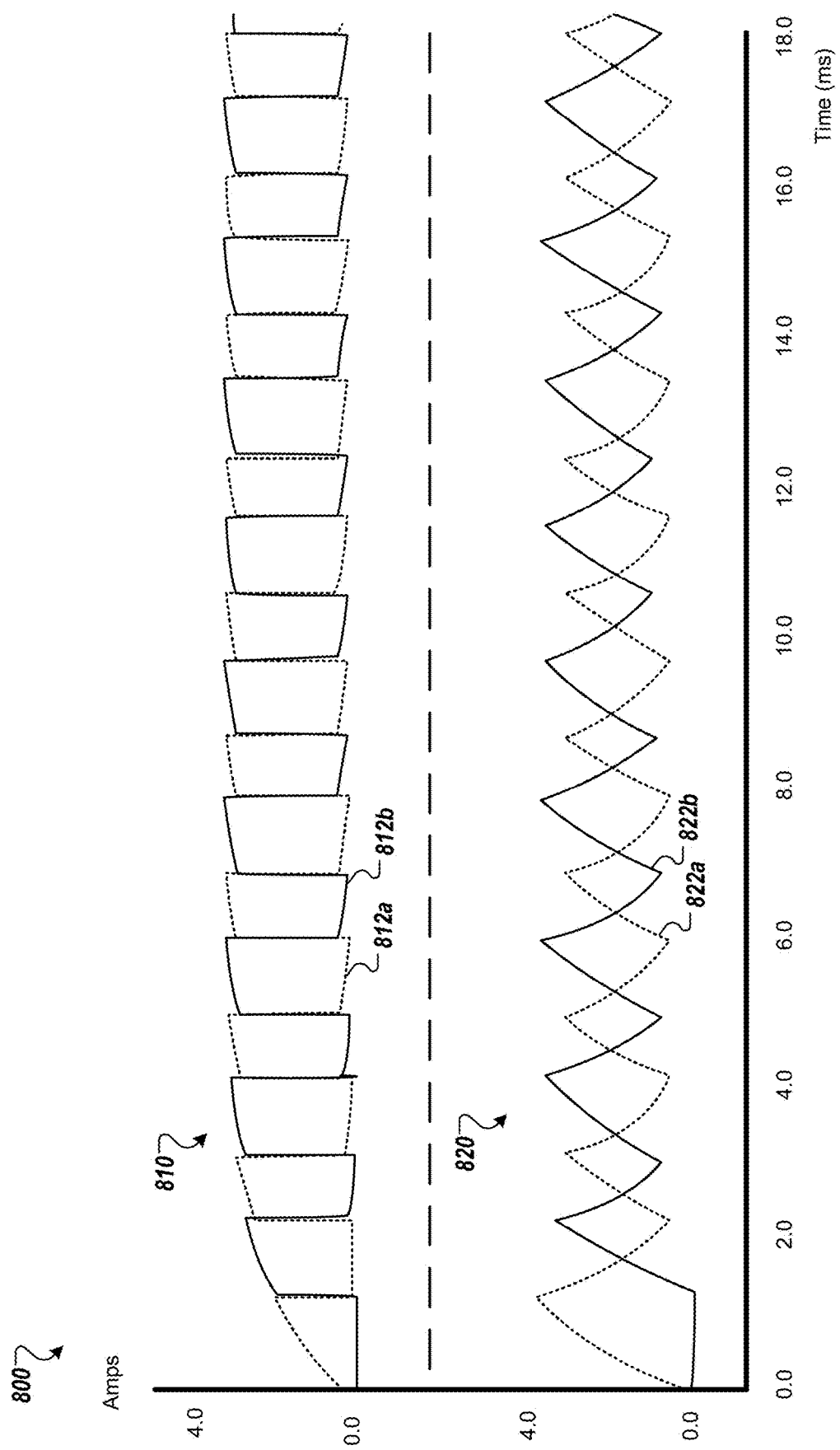

FIGS. 6-8 are charts of example motor driver electrical waveforms.

FIG. 6 is a chart 600 that shows an example of a current waveform 610 that can be produced by the example circuit 500 of FIG. 5. FIG. 6 also shows an example of a current waveform 620 that can be produced by known circuits, such as the circuit 400 of FIG. 4.

It can be observed that both of the waveform 610 and the waveform 620 have roughly the same start-up behavior, since there is no energy stored in their respective motor coils yet. After the first coils stores energy, the effect of the energy recirculation can be observed the waveform 610 rising faster than the waveform 620, and with less ripple. In the illustrated example, both cases had the same 24 v supply voltage. The faster rise times of the waveform 610 are due to the energy stored in the coils being transferred quickly to the complementary coil during switching edges, which allows the coils (or windings or inductances) to have more initial energy and therefore be further along in the first-order $1-e^{-t/\tau}$ curve, and therefore exhibit less current ripple.

FIG. 7 is a chart 700 that shows another example of a current waveform 710 that can be produced by the example circuit 500 of FIG. 5. FIG. 7 also shows an example of a current waveform 720 that can be produced by known circuits, such as the circuit 400 of FIG. 4. The chart 700 shows example of the ripple currents after the supply voltages (e.g., of the power bus 412 and 512) have been adjusted to match peak current values (e.g., at the end of the on-time cycles), as represented by line 730. The waveform 710 has a ripple of about 141 mA, as measured between initial current values represented by line 732, and the peak current values 730. By contrast, the waveform 720 has a ripple of about 1.57 A between initial current values represented by line 734, and the peak current values 730. The ripple of the example circuit 500 exhibits ripple that is a factor of about 11× less than the ripple exhibited by the known circuit 400. In implementations in which power supplies adjusted to accomplish equivalent average current instead of peak current, the factor of ripple reduction provided by the circuit 500 can be be even greater.

FIG. 8 is a chart 800 that shows another example of a current waveform pair 810 that can be produced by the example circuit 500 of FIG. 5. FIG. 8 also shows an example of a current waveform pair 820 that can be produced by known circuits, such as the circuit 400 of FIG. 4. The current waveform pair 810 includes a waveform 812*a* and a waveform 812*b*. In some implementations, the waveforms 812*a* and 812*b* can represent example currents of windings within a motor phase (e.g., for the purpose of more clearly illustrating the reduced ripple provided by the circuit 500). In some implementations, the waveform 812*a* can be an example of the current waveform across the example winding 501*a*, and the waveform 812*b* can be an example of the current waveform across the example winding 501*b*. The current waveform pair 820 includes a waveform 822*a* and a waveform 822*b*. In some implementations, the waveform 822*a* can be an example of the current waveform across the example winding 401*a*, and the waveform 822*b* can be an example of the current waveform across the example winding 401*b*. In general, the chart 800 illustrates an example improvement in ripple and energy transfer provided by the circuit 500 when compared to the circuit 400.

Figure 9:
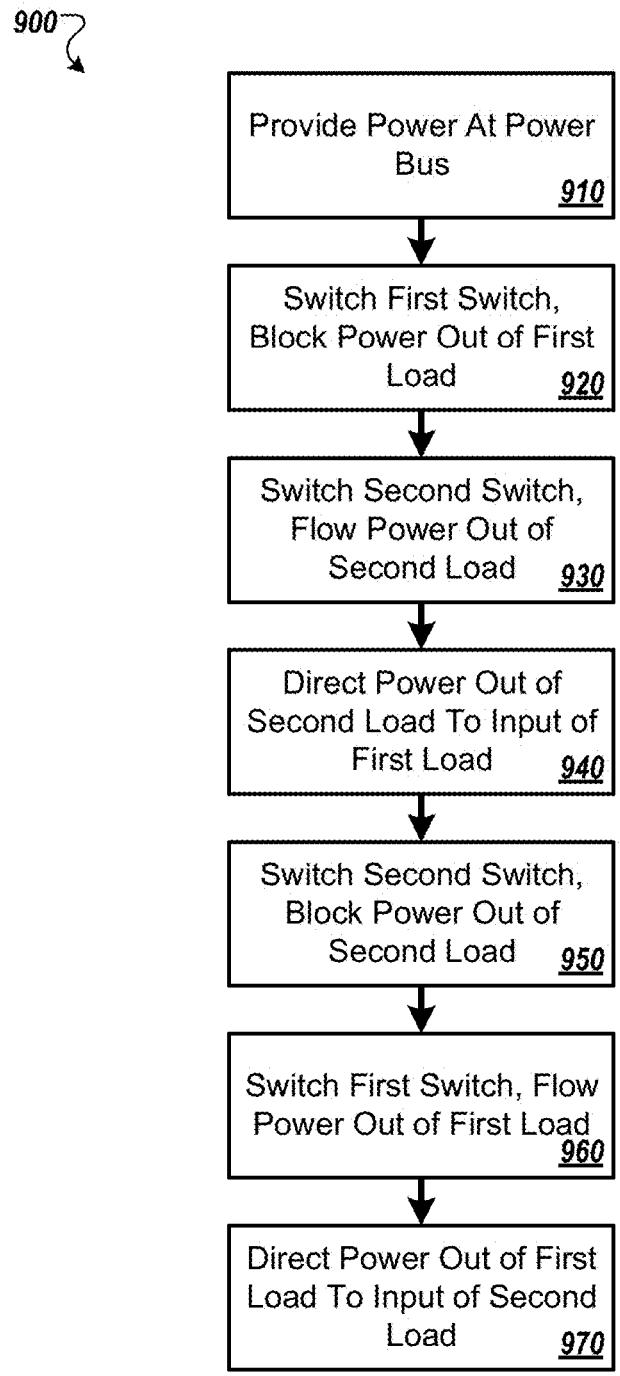
FIG. 9 is a flow diagram of an example process in accordance with some embodiments.

FIG. 9 is a flow diagram of an example process 900 in accordance with some embodiments. In some implementations, the process 900 can be performed by the example circuit 500 of FIG. 5.

At 910, power is provided at a power bus to a first output and to a second output. For example, power can be provided by the power supply 510 at the power bus 512 to the load output port 514*a* and the load output port 514*b*.

At 920, a first switch is switched to block power flow out of the first electrical load to a low electrical potential bus. For example, the switch 530*a* can be switched off to stop the power flowing out from the winding 501*a* to the low electrical potential bus 520.

At 930, a second switch is switched to permit power from the power bus to flow from the second output, through a second electrical load electrically connected to the second output, to the low electrical potential bus. For example, the switch 530*b* can be switched on to permit power from the power bus 512 to flow through the winding 501*b* to the low electrical potential bus 520.

At 940, a first snubber circuit directs power flow out of the first electrical load to the second output. For example, the branch 551*a* of the snubber circuit 550 conducts residual energy flowing in though the load input port 516*a* and blocked by the switch 530*a*, to the load output port 514*b*.

In some implementations, the first snubber circuit can include a resistor and a diode in series electrical connection with the resistor. For example, the branch 551*a* includes the diode 552*a* and the current limiting resistor 554*a*. In some implementations, directing, by the first snubber circuit, power flow out of the first electrical load to the second output can include permitting, by the diode, power flow from the first electrical load at a first input to the second output, and preventing, by the diode, power flow from the second output to the first input. For example, the diode 552*a* can permit one-way current flow from the load input port 516*a* to the load output port 514*b*.

At 950, the second switch is switched to block power flow out of the second electrical load to the low electrical potential bus. For example, the switch 530*b* can be switched to block power flowing in through the load input port 516*b* from flowing to the low electrical potential bus 520.

At 960, the first switch is switched to permit power from the power bus to flow from the first output, though the first electrical load, to the low electrical potential bus. For example, the switch 530*a* is switched to permit power to flow from the load input port 516*a* to the low electrical potential bus 520.

At 970, a second snubber circuit directs power flow out of the second electrical load to the first output. For example, the branch 551*b* of the snubber circuit 550 conducts residual energy flowing in though the load input port 516*b* and blocked by the switch 530*b*, to the load output port 514*a*. In some implementations, power flow out of the first electrical load to the first output can at least partly be current flow caused by inductance of the first inductive load, and power flow out of the second electrical load to the second output can at least partly be current flow caused by inductance of the second inductive load.

In some implementations disclosed herein, the first snubber circuit can include a resistor and a diode in series electrical connection with the resistor. For example, the branch 551*b* includes the diode 552*b* and the current limiting resistor 554*b*. In some implementations, directing, by the second snubber circuit, power flow out of the second electrical load to the first output can include permitting, by the diode, power flow from the second electrical load at a second input to the first output, and preventing, by the diode, power flow from the first output to the second input. For example, the diode 552*b* can permit one-way current flow from the load input port 516*b* to the load output port 514*a*.

In some implementations disclosed herein, the process 900 can also include preventing backflow of current from the first snubber circuit to the power bus, and preventing backflow of current from the second snubber circuit to the power bus. For example, the diodes 518*a* and 518*b* can prevent backflow of power from the snubber circuit 550 to the power bus 512.

In some implementations disclosed herein, the first electrical load can be a first inductive electrical load, and the second electrical load can be a second inductive electrical load. For example, the winding 501*a* is an electrical load that includes the coil 502*a*, which is an inductive electrical load, and the winding 501*b* is an electrical load that includes the coil 502*b*, which is another inductive electrical load. In some implementations, switching the first switch to permit power from the power bus to flow from the first output, through a first electrical load electrically connected to the first output, to the low electrical potential bus can include energizing the first inductive electrical load. For example, when current flows through the winding 501*a*, the coil 502*a* can become energized. In some implementations, switching the second switch to permit power from the power bus to flow from the second output, through a second electrical load electrically connected to the second output, to the low electrical potential bus can include energizing the second inductive electrical load. For example, when current flows through the winding 501*b*, the coil 502*b* can become energized.

In some embodiments disclosed herein, the first electrical load can be a first winding of a stepper motor, and the second electrical load can be a second winding of the stepper motor. For example, the winding 501*a* can be all or part of the winding 320a of the stepper motor 300, and the winding 501b can be all or part of the winding 320b. In some implementations, switching the first switch to permit power from the power bus to flow from the first output, though the first electrical load, to the low electrical potential bus can include energizing the first winding, and switching the second switch to permit power from the power bus to flow from the second output, through a second electrical load electrically connected to the second output, to the low electrical potential bus can include energizing the second winding. For example, the switches 530a and 530b can be switched to energize the windings 501a and 501b, which can be the windings 320a and 320b.

In some implementations disclosed herein, the process 900 can also include controllably switching the first switch and the second switch to urge rotation of the stepper motor in a first direction, actuating, by the stepper motor, a tube clamp device configured to releasably receive a tube, and adjusting, based on the actuation, an amount of compression applied to the tube by the tube clamp device. For example, the example circuit 500 can be used to actuate the example stepper motor 300 of FIG. 3, which can be configured to actuate the example occluder device 170 of FIGS. 1 and 2. The stepper motor 300 can be operated to control an amount of compression applied to the tube 122, and thereby modulate the flow of fluid through the tube 122.

While the examples given in this specification generally discuss the concept of recirculating energy from one winding of a motor phase to another winding of the same motor phase, other embodiments exist. For example, the processes and systems described herein can be modified to recirculate energy from a winding of a motor phase to another winding in another motor phase. In another example, the processes and systems described herein can be modified to recirculate energy from any appropriate energy storage device (e.g., inductor, inductive load, capacitor, capacitive load) to any other appropriate energy storage device.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A tube occluder system comprising:
   a tube clamp device configured to releasably receive a tube;
   a stepper motor having a first winding and a second winding, and arranged to adjust an amount of compression applied to the tube by the tube clamp device; and
   a drive system electrically coupled to the stepper motor and comprising:
   a first port configured to electrically connect to a first winding input of the first winding;
   a second port configured to electrically connect to a first winding output of the first winding;
   a third port configured to electrically connect to a second winding input of a second winding;
   a fourth port configured to electrically connect to a second winding output of the second winding;
   a first snubber circuit in electrical communication between the second port and the third port; and
   a second snubber circuit in electrical communication between the fourth port and the first port.

2. The tube occluder system of claim 1, wherein the first snubber circuit comprises a resistor and a diode in series electrical connection with the resistor, and the diode is configured to pass current from the second port to the third port, and prevent current flow from the third port to the second port.

3. The tube occluder system of claim 2, wherein the second snubber circuit comprises a resistor and a second diode in series electrical connection with the second resistor, and the second diode is configured to pass current from the fourth port to the first port, and prevent current flow from the first port to the fourth port.

4. The tube occluder system of claim 1, further comprising a power bus, a first diode configured to pass current from the power bus to the first port, and a second diode configured to pass current from the power bus to the third port.

5. The tube occluder system of claim 1, further comprising a low electrical potential power bus, a first switch configured to controllably connect the second port to the low electrical potential power bus, and a second switch configured to controllably connect the fourth port to the low electrical potential power bus, and at least one resistor configured to limit current flow from the second port to the low electrical potential power bus and to limit current flow from the third port to the low electrical potential power bus.

6. A method of recirculating energy in a stepper motor, the method comprising:
   providing power at a power bus to a first output and to a second output;
   flowing power through a first electrical load electrically connected to the first output;
   switching a first switch to block power flow out of the first electrical load to a low electrical potential bus;
   switching a second switch to permit power from the power bus to flow from the second output, through a second electrical load electrically connected to the second output, to the low electrical potential bus;

directing, by a first snubber circuit, power flow out of the first electrical load to the second output;
switching the second switch to block power flow out of the second electrical load to the low electrical potential bus;
switching the first switch to permit power from the power bus to flow from the first output, though the first electrical load, to the low electrical potential bus; and
directing, by a second snubber circuit, power flow out of the second electrical load to the first output.

7. The method of claim 6, further comprising:
preventing backflow of current from the first snubber circuit to the power bus; and
preventing backflow of current from the second snubber circuit to the power bus.

8. The method of claim 6, wherein the first snubber circuit comprises a resistor and a diode in series electrical connection with the resistor, wherein directing, by the first snubber circuit, power flow out of the first electrical load to the second output comprises:
permitting, by the diode, power flow from the first electrical load at a first input to the second output; and
preventing, by the diode, power flow from the second output to the first input.

9. The method of claim 8, wherein the second snubber circuit comprises a second resistor and a second diode in series electrical connection with the second resistor, wherein directing, by the second snubber circuit, power flow out of the second electrical load to the first output comprises:
permitting, by the second diode, power flow from the second electrical load at a second input to the first output; and
preventing, by the second diode, power flow from the first output to the second input.

10. The method of claim 6, wherein:
the first electrical load comprises a first inductive electrical load;
the second electrical load comprises a second inductive electrical load;
switching the first switch to permit power from the power bus to flow from the first output, though the first electrical load, to the low electrical potential bus comprises energizing the first inductive electrical load; and
switching the second switch to permit power from the power bus to flow from the second output, through a second electrical load electrically connected to the second output, to the low electrical potential bus comprises energizing the second inductive electrical load.

11. The method of claim 10, wherein power flow out of the first electrical load to the first output at least partly comprises current flow caused by inductance of the first inductive load, and power flow out of the second electrical load to the second output at least partly comprises current flow caused by inductance of the second inductive load.

12. The method of claim 6, wherein:
the first electrical load comprises a first winding of a stepper motor; and
the second electrical load comprises a second winding of the stepper motor.

13. The method of claim 12, wherein:
switching the first switch to permit power from the power bus to flow from the first output, though the first electrical load, to the low electrical potential bus comprises energizing the first winding; and
switching the second switch to permit power from the power bus to flow from the second output, through a second electrical load electrically connected to the second output, to the low electrical potential bus comprises energizing the second winding.

14. The method of claim 13, further comprising:
controllably switching the first switch and the second switch to urge rotation of the stepper motor in a first direction;
actuating, by the stepper motor, a tube clamp device configured to releasably receive a tube; and
adjusting, based on the actuation, an amount of compression applied to the tube by the tube clamp device.

15. An electrical drive system comprising:
a first port configured to electrically connect to a first load input of a first electrical load;
a second port configured to electrically connect to a first load output of the first electrical load;
a third port configured to electrically connect to a second load input of a second electrical load;
a fourth port configured to electrically connect to a second load output of the second electrical load;
a first snubber circuit in electrical communication between the second port and the third port; and
a second snubber circuit in electrical communication between the fourth port and the first port.

16. The system of claim 15, wherein:
the first snubber circuit comprises a first resistor and a first diode in series electrical connection with the first resistor, and the first diode is configured to pass current from the second port to the third port, and prevent current flow from the third port to the second port; and
the second snubber circuit comprises a second resistor and a second diode in series electrical connection with the second resistor, and the second diode is configured to pass current from the fourth port to the first load output port, and prevent current flow from the first load output port to the fourth port.

17. The system of claim 15, further comprising a power bus, a first diode configured to pass current from the power bus to the first port, and a second diode configured to pass current from the power bus to the third port.

18. The system of claim 15, further comprising a low electrical potential power bus, a first switch configured to controllably connect the second port to the low electrical potential power bus, and a second switch configured to controllably connect the fourth port to the low electrical potential power bus, and at least one resistor configured to limit current flow from the second port to the low electrical potential power bus and to limit current flow from the third port to the low electrical potential power bus.

19. The system of claim 15, wherein at least one of the first electrical load and the second electrical load is an inductive electrical load.

20. The system of claim 15, wherein the first electrical load is a first winding of a stepper motor, and the second electrical load is a second winding of the stepper motor.

* * * * *

UNITED STATES PATENT AND TRADEMARK OFFICE
CERTIFICATE OF CORRECTION

PATENT NO. : 11,724,098 B2  
APPLICATION NO. : 16/777533  
DATED : August 15, 2023  
INVENTOR(S) : James Bradley Atherton Page 1 of 1

It is certified that error appears in the above-identified patent and that said Letters Patent is hereby corrected as shown below:

In the Claims

In Column 18, Line 39, in Claim 16, after first delete "load output";

In Column 18, Line 40, in Claim 16, after first delete "load output".

Signed and Sealed this  
Third Day of October, 2023

Katherine Kelly Vidal  
*Director of the United States Patent and Trademark Office*